United States Patent
Mougin et al.

(10) Patent No.: US 8,722,028 B2
(45) Date of Patent: *May 13, 2014

(54) ETHYLENIC COPOLYMERS, COMPOSITIONS AND METHODS OF THE SAME

(71) Applicant: L'Oreal, Paris (FR)

(72) Inventors: Nathalie Mougin, Paris (FR); Gwenaelle Jegou, Saint Michel sur Orge (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/039,305

(22) Filed: Sep. 27, 2013

(65) Prior Publication Data

US 2014/0023608 A1 Jan. 23, 2014

Related U.S. Application Data

(62) Division of application No. 11/179,469, filed on Jul. 13, 2005.

(60) Provisional application No. 60/590,440, filed on Jul. 23, 2004.

(30) Foreign Application Priority Data

Jul. 13, 2004 (FR) .................................... 04 51512

(51) Int. Cl.
 *A61K 8/00* (2006.01)
(52) U.S. Cl.
 USPC .......................................................... 424/70.1
(58) Field of Classification Search
 None
 See application file for complete search history.

(56) References Cited

U.S. PATENT DOCUMENTS

| | | | |
|---|---|---|---|
| 4,800,220 A | 1/1989 | Ribba | |
| 5,362,415 A | 11/1994 | Egraz et al. | |
| 5,502,136 A | 3/1996 | Zhong et al. | |
| 6,193,961 B1 | 2/2001 | Liu et al. | |
| 6,645,476 B1 | 11/2003 | Morschhauser et al. | |
| 6,833,419 B2 | 12/2004 | Morschhauser et al. | |
| 6,878,683 B2 | 4/2005 | Neumann et al. | |
| 6,891,011 B2 | 5/2005 | Morschhauser et al. | |
| 6,964,995 B2 | 11/2005 | Morschhauser et al. | |
| 2003/0148915 A1 | 8/2003 | Neumann et al. | |
| 2004/0091444 A1 | 5/2004 | Loffler et al. | |
| 2004/0096409 A1 | 5/2004 | Loeffler et al. | |
| 2004/0097657 A1 | 5/2004 | Morschhaeuser et al. | |
| 2004/0109835 A1 | 6/2004 | Loffler et al. | |
| 2004/0109836 A1 | 6/2004 | Loffler et al. | |
| 2004/0109838 A1 | 6/2004 | Morschhuser et al. | |
| 2004/0115148 A1 | 6/2004 | Loffler et al. | |
| 2004/0115149 A1 | 6/2004 | Loffler et al. | |
| 2004/0115157 A1 | 6/2004 | Loffler et al. | |
| 2004/0116628 A1 | 6/2004 | Morschhauser et al. | |
| 2004/0116634 A1 | 6/2004 | Morschhaeuser et al. | |
| 2004/0141937 A1 | 7/2004 | Loffler et al. | |
| 2004/0167304 A1 | 8/2004 | Morschhauser et al. | |
| 2005/0032998 A1 | 2/2005 | Morschhaeuser et al. | |
| 2005/0089536 A1 | 4/2005 | Loffler et al. | |
| 2005/0232887 A1 | 10/2005 | Morschhuser et al. | |
| 2006/0217285 A1 | 9/2006 | Destarac | |

FOREIGN PATENT DOCUMENTS

| | | |
|---|---|---|
| EP | 3235 A1 | 8/1979 |
| EP | 0013836 A1 | 8/1980 |
| EP | 0324568 A2 | 7/1989 |
| EP | 0577526 A1 | 1/1994 |
| EP | 0372546 B1 | 6/1995 |
| EP | 0 931 799 A2 | 7/1999 |
| EP | 0931776 A1 | 7/1999 |
| EP | 0995791 A1 | 4/2000 |
| EP | 1069142 A1 | 1/2001 |
| EP | 1136508 A1 | 9/2001 |
| EP | 1256621 A1 | 11/2002 |
| JP | 03185184 A | 8/1991 |
| JP | 07-285831 A | 10/1995 |
| JP | 09040837 A | 2/1997 |
| JP | 09078050 A | 3/1997 |
| JP | 11268939 A | 10/1999 |
| JP | 2000024691 A | 1/2000 |
| JP | 2000-302649 A | 10/2000 |
| JP | 2002-011338 A | 1/2002 |
| JP | 2002179449 A | 6/2002 |
| JP | 2002-284627 A | 10/2002 |
| JP | 2002-322219 A | 11/2002 |
| JP | 2002-327102 A | 11/2002 |
| JP | 2003-500522 A | 1/2003 |
| JP | 2003-55164 | 2/2003 |
| JP | 2003081739 A | 3/2003 |
| JP | 2003165804 A | 6/2003 |
| JP | 2003-535962 A | 12/2003 |

(Continued)

OTHER PUBLICATIONS

Machine translation of JP 3185184A, May 2013.
http://www.fitzchem.com/pdf/Cognis_Bisomer_Monomers.pdf, accessed Jun. 17, 2009.
Machine translation of JP 2002179449 A.
Machine translation of JP 2003165804 A.
French Search Report for FR 0451512, dated Feb. 2, 2005.
European Search Report for EP 05 29 1089, dated Mar. 1, 2006.
English language abstract of JP 7-285831, Oct. 31, 1995.

(Continued)

*Primary Examiner* — Paul Dickinson
(74) *Attorney, Agent, or Firm* — Novak Druce Connolly Bove + Quigg LLP

(57) ABSTRACT

The present disclosure relates to novel ethylenic copolymers comprising from 10% to 80% by weight, of at least one monomer of polyethylene glycol (meth)acrylate type, from 20% to 90% by weight, of at least one anionic monomer, and from 0% to 70% by weight, at least one additional nonionic hydrophilic monomer. The disclosure also relates to a composition, such as cosmetic or pharmaceutical compositions, comprising the copolymers and to a method of using the same.

34 Claims, No Drawings

(56) References Cited

FOREIGN PATENT DOCUMENTS

| WO | WO-9716463 | A1 | 5/1997 |
| WO | WO-0071651 | A2 | 11/2000 |
| WO | WO-0196007 | A1 | 12/2001 |
| WO | WO-02/09656 | A2 | 2/2002 |
| WO | WO-02/44267 | A2 | 6/2002 |
| WO | WO-0244230 | A2 | 6/2002 |
| WO | WO-0244231 | A1 | 6/2002 |
| WO | WO-03062288 | A1 | 7/2003 |
| WO | WO-03/075867 | A1 | 9/2003 |
| WO | WO-2004044023 | A1 | 5/2004 |

OTHER PUBLICATIONS

English language abstract of JP 2000-302649, Oct. 31, 2000.
English language abstract of JP 2002-284627, Oct. 3, 2002.
English language abstract of JP 2002-322219, Nov. 8, 2002.
English language abstract of JP 2003-55164, Feb. 26, 2003.

ETHYLENIC COPOLYMERS, COMPOSITIONS AND METHODS OF THE SAME

CROSS-REFERENCE TO RELATED APPLICATIONS

This Application is a Divisional of U.S. patent application Ser. No. 11/179,469, filed Jul. 13, 2005, and claims the benefit of French Patent Application No. 04 51512, filed Jul. 13, 2004 and also claims the benefit of U.S. Provisional Patent Application No. 60/590,440, filed Jul. 23, 2004. The disclosures of the aforementioned applications are incorporated herein in their entirety by reference.

The present disclosure relates to novel polymers, to their use, in, for example, cosmetics, and to compositions comprising them.

It is known to employ polymers in the cosmetics field, and for example, in the hair field, for purposes such as contributing hold or styling to the hair.

Numerous cosmetic compositions, and for example, hair compositions referred to as hair styling compositions, which are provided in the form of aerosols (sprays), gels, foams or shampoos, comprise resins or polymers.

For example, U.S. Pat. No. 6,193,961 from ISP discloses a homogeneous terpolymer of N-vinyllactam, such as of N-vinylpyrrolidone or of N-vinylcaprolactam, of dimethylaminoalkyl acrylate or of dimethylaminoalkylacrylamide and of a polysiloxane monomer.

U.S. Pat. No. 5,502,136 relates to a process for the preparation of copolymers of vinylpyrrolidone and of vinyl acetate by radical polymerization.

However, it was found that these polymers may not exhibit satisfactory removal on shampooing.

In the field of hair compositions referred to as 'leave-in' compositions, such as styling products of styling spray, gel or lacquer type, there is a continual search for good styling polymers.

For example, International Patent Application Publication WO 2002/09656 discloses hydrophobic polymers based on butyl acrylate, which contribute a repositionable styling effect. European Patent Application Publication No. EP 1 201 223 discloses copolymers based on alkyl (meth)acrylates which may make it possible to style and restyle the hair at will. However, in both these cases, the cosmetic quality to the touch may be inadequate.

Thus, it would be desirable to find polymers which provide styling but at the same time also provide at least one acceptable cosmetic quality and are easily removed on shampooing.

The present disclosure seeks to provide polymers capable of contributing a true styling effect to the compositions, while retaining an acceptable cosmetic quality and for example, good removal on shampooing.

After much research, the present inventors have found that the use of polymers comprising, inter alia, monomers of the polyethylene glycol (meth)acrylate type as defined below may make possible the preparation of styling compositions having an appropriate cosmetic quality.

Polymers comprising polyethylene glycol (meth)acrylate (PEGM) units may be provided for in the prior art.

For example, European Patent Application Publication No. EP 372 546 discloses copolymers based on PEGM and on monomers of ($C_1$-$C_8$ alkyl)(meth)acrylamide type which may comprise cationic monomers. These cationic polymers, however, are not always easily removed on rinsing. Furthermore, they may not make it possible to produce suitable cosmetic effects, such as a deposited layer on the hair, which is sufficient to contribute the desired properties.

Japanese Patent Application Publication JP2002-322219 discloses polymers comprising PEGM units in combination with hydrophobic monomers based on polypropylene glycol (PPO) or on poly(tetramethylene oxide) and cationic monomers. These polymers thus comprise hydrophobic monomers and they may not make it possible to obtain satisfactory cosmetic properties.

In addition, Japanese Patent Application Publication JP2002-284627 discloses a composition comprising cationic polymers wherein monomers of PEG type are combined with monomers comprising quaternary amine units. In this instance, the presence of quaternary units may result, during application, in extra deposition, which may lead, in some cases, to a poor cosmetic quality and may result in difficulties in removal on shampooing.

Furthermore, Japanese Patent Application Publication JP2003-055164 discloses polymers comprising units of the PEGM type; however, these polymers are crosslinked, which may make it difficult to control their synthesis and their removal on shampooing.

Japanese Patent Application Publication JP2000-302649 discloses a hair composition comprising a polymer, which comprises cationic or amphoteric monomers, monomers with a polyether group, such as PEGM or PPO type, and optional monomers which may be mainly hydrophobic (stearyl methacrylate).

In addition, Japanese Patent No. JP07-285831 also discloses hair compositions comprising a polymer which comprises monomers of PEGM type in combination with ionic, cationic or amphoteric monomers and additional monomers, mainly hydrophobic, of $C_1$-$C_{24}$ alkyl (meth)acrylate type.

However, the presence of hydrophobic monomers of butyl acrylate or stearyl acrylate type may not make it possible to obtain suitable cosmetic properties, such as a satisfactory good cosmetic quality and satisfactory removal on shampooing.

International Patent Application Publication WO 03/075867 is also known, which discloses linear block copolymers comprising a poly(alkylene glycol) block framed by two ethylenic blocks. These polymers may exhibit the drawback of having a central block of poly(alkylene glycol) type with a high mass which confers high crystallinity on the polymer, which may result in opaque products and/or products exhibiting a greasy nature.

Furthermore, in all the polymers disclosed in these documents, the ionic monomers may be mainly cationic monomers, which may form a deposited layer on the hair when they are brought into the presence of an anionic surfactant. In some cases, for example, the case of leave-in styling products of lacquer type, it may be desirable to have available compositions which may be easily removed, such as on washing, for example, with a shampoo comprising an anionic surfactant.

It is thus desirable to have polymers comprising PEGMs and anionic units in order to obtain a satisfactory deposited layer of polymer on the hair.

The present disclosure demonstrates novel polymers which may make it possible to contribute a styling and conditioning effect to hair cosmetic products while also being easy to remove, for example, on shampooing.

Surprisingly, the polymers according to the present disclosure have desirable cosmetic properties, for example, when applied in a formulation of lacquer or shampoo type. For example, it has been found that the hair easily disentangles during shampooing and may exhibit softness after application; after drying, the compositions according to the disclosure also may make possible a desirable reshaping of the hair.

In addition, the application of these presently disclosed compositions may make it possible to obtain a styling effect, which may be easily removed on shampooing.

Finally, the polymers according to the disclosure may be easily formulated, for example, in a pump-action spray.

Without being committed to the present explanation, it may be thought that these properties may, for example, be due to the presence of PEG (meth)acrylate (PEGM) units within the polymer chain, which units largely contribute to the effect obtained.

The present disclosure thus relates to an ethylenic copolymer comprising:

a) from 10% to 80% by weight, relative to the total weight of the copolymer, of at least one monomer of formula (I) as defined below;

b) from 20% to 90% by weight, relative to the total weight of the copolymer, of at least one anionic monomer chosen from maleic anhydride and monomers of formula (II) as defined below, and c) optionally from 0% to 70% by weight, relative to the total weight of the copolymer, of at least one nonionic hydrophilic monomer.

Another embodiment of the present disclosure is a composition comprising, in a physiologically acceptable medium, at least one such copolymer.

The polymers disclosed herein may generally be conveyed in water, that is to say which are soluble or dispersible in water, which may make it possible to employ them in cosmetic compositions, such as skin care or hair compositions, generally with an aqueous base.

As used herein, the term "water-soluble" or "soluble in water" is understood to mean that the polymer forms a clear solution in water, in a proportion of at least 5% by weight, at 25° C.

As used herein, the term "water-dispersible" or "dispersible in water" means that the polymer forms in water, at a concentration of 5% by weight, at 25° C., a stable suspension or dispersion of fine, generally spherical, particles. The mean size of the particles constituting the dispersion may be, for example, less than 1 µm and, more generally, ranges from 5 nm to 400 nm, such as from 10 nm to 250 nm. These particle sizes may be measured by light scattering techniques.

As used herein, the term "cyclic radical" refers to a monocyclic or polycyclic radical which may itself exist in the form of at least one ring chosen from saturated and unsaturated rings which are optionally substituted (for example, cyclohexyl, cyclodecyl, benzyl or fluorenyl) but also a radical which comprises at least one of the rings (for example, p-(tert-butyl)cyclohexyl or 4-hydroxybenzyl).

As used herein, the term "saturated and/or unsaturated radical" refers to fully saturated radicals, fully unsaturated radicals, including aromatic radicals, and radicals comprising at least one bond chosen from double and triple bonds, the remainder of the bonds being single bonds.

The ethylenic copolymer according to the present disclosure thus comprises at least one monomer of formula (I), which may be present alone or as a mixture:

$$H_2N=C\begin{matrix}R_1\\(Z)_x-(R_2)_m-(CH_2CH_2O)_n-R_3\end{matrix}$$ (I)

wherein:

$R_1$ is chosen from a hydrogen atom and linear and branched hydrocarbon radicals $C_pH_{2p+1}$ wherein p is an integer ranging from 1 to 12 inclusive;

Z is a divalent group chosen from —COO—, —CONH—, —CONCH$_3$—, —OCO—, —O—, —SO$_2$—, —CO—O—CO—, and —CO—CH$_2$—CO—;

x is chosen from 0 and 1;

$R_2$ is chosen from linear, branched and cyclic, saturated and unsaturated, optionally aromatic, divalent hydrocarbon radicals having from 1 to 30 carbon atoms which optionally comprise from 1 to 18 heteroatoms chosen from O, N, S, F, Si, and P;

m is chosen from 0 and 1;

n is an integer ranging from 3 to 300 inclusive;

$R_3$ is chosen from a hydrogen atom and linear, branched and cyclic, saturated and unsaturated, optionally aromatic, hydrocarbon radicals having from 1 to 30 carbon atoms, which optionally comprises from 1 to 20 heteroatoms chosen from O, N, S, F, Si, and P; and salts thereof.

For example, in at least one embodiment, $R_1$ is chosen from methyl, ethyl, propyl, and butyl radicals. In at least one further embodiment, $R_1$ is chosen from hydrogen and a methyl radical.

In at least one embodiment, Z is chosen from —COO— and —CONH—.

In at least one embodiment, x is equal to 1.

In the $R_2$ radical, the heteroatom or heteroatoms, when they are present, may be inserted into the chain of the $R_2$ radical or the $R_2$ radical may be substituted by at least one group comprising them, such as hydroxyl or amino (NH$_2$, NHR' or NR'R", with R' and R", which may be identical or different, chosen from linear and branched $C_1$-$C_{22}$ alkyls, such as methyl or ethyl).

For example, $R_2$ comprises a radical chosen from:

an alkylene radical, such as methylene, ethylenic, propylene, n-butylene, isobutylene, tert-butylene, n-hexylene, n-octylene, n-dodecylene, n-octadecylene, n-tetradecylene or n-docosenylene;

a phenylene radical $C_6H_4$— (ortho, meta or para) optionally substituted by a $C_1$-$C_{12}$ alkyl radical optionally comprising from 1 to 25 heteroatoms chosen from O, N, S, F, Si, and P; or a benzylene radical —$C_6H_4$—$CH_2$— optionally substituted by a $C_1$-$C_{12}$ alkyl radical optionally comprising from 1 to 25 heteroatoms chosen from O, N, S, F, Si, and P;

a pyridinium radical of formula:

$$\begin{matrix}R'_1 & & R'_3\\ & \diagdown & \\ & N^+ & \\ R'_2 & | & R'_4\end{matrix}$$

wherein $R'_1$ to $R'_4$, which may be identical or different, are chosen from H and $C_1$-$C_{12}$ alkyl radicals optionally comprising from 1 to 8 heteroatoms chosen from O, N, S, F, Si, and P; in at least one embodiment, $R'_1$ to $R'_4$ may independently be chosen from methyl and ethyl;

a radical of formula —CH$_2$—O—CO—O—, —CH$_2$—CH$_2$—O—CO—O—, —CH$_2$—CO—O—, —CH$_2$—CH$_2$—CO—O—, —CH$_2$—O—CO—NH—, —CH$_2$—CH$_2$—O—CO—NH—; —CH$_2$—NH—CO—NH— and —CH$_2$—CH$_2$—NH—CO—NH—, —CH$_2$—CHOH—, —CH$_2$—CH$_2$—CHOH—, —CH$_2$—CH$_2$—CH(NH$_2$)—, —CH$_2$—CH(NH$_2$)—, —CH$_2$—CH$_2$—CH(NHR')—, —CH$_2$—CH(NHR')—, —CH$_2$—CH$_2$—CH(NR'R")—, —CH$_2$—CH(NR'R")—, —CH$_2$—CH$_2$—CH$_2$—NR'—, —CH$_2$—CH$_2$—CH$_2$—O—, and —CH$_2$—CH$_2$—CHR'—O— wherein R' and R" are chosen from linear and branched C$_1$-C$_{22}$ alkyls optionally comprising from 1 to 12 heteroatoms chosen from O, N, S, F, Si, and P;

and mixtures thereof.

For example, in at least one embodiment, n ranges from 5 and 200 inclusive and further for example, from 7 to 100 inclusive, such as from 9 to 50 inclusive.

Further for example, in at least one embodiment, $R_3$ is chosen from a hydrogen atom; benzyl and phenyl radicals optionally substituted by a C$_1$-C$_{12}$ alkyl radical optionally comprising from 1 to 25 heteroatoms chosen from O, N, S, F, Si, and P; and C$_1$-C$_{30}$, such as C$_1$-C$_{22}$, further for example, C$_2$-C$_{16}$, alkyl radicals optionally comprising from 1 to 18 heteroatoms chosen from O, N, S, F, Si, and P.

These benzyl, phenyl and alkyl radicals optionally comprise, for example, a functional group chosen from the following functional groups:

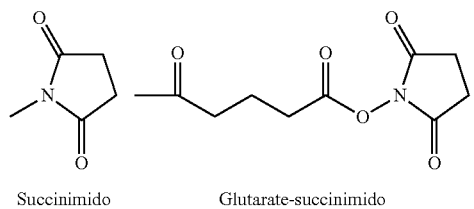

Succinimido        Glutarate-succinimido

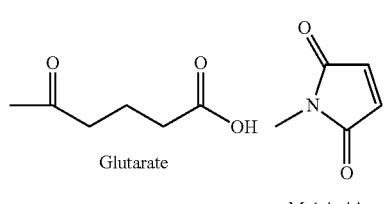

Glutarate          Maleimido

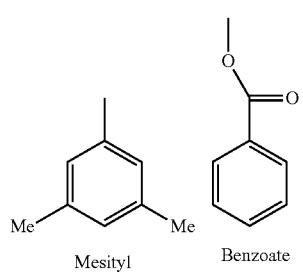

Mesityl       Benzoate

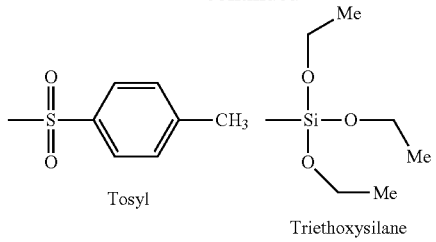

Tosyl             Triethoxysilane

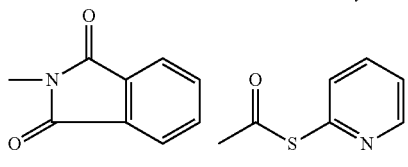

Phthalimide          Thioester

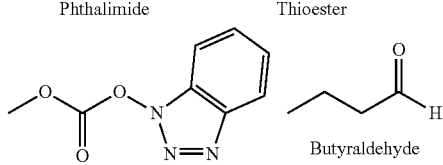

Benzotriazole carbonate       Butyraldehyde

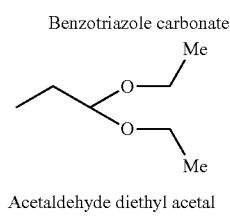

Acetaldehyde diethyl acetal

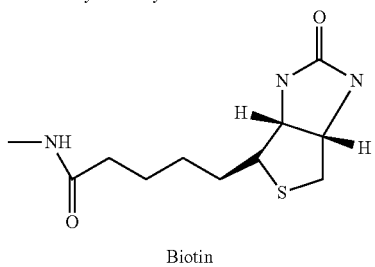

Biotin

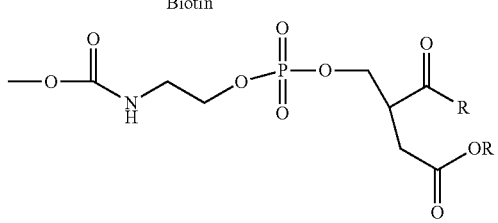

Phospholipid
with R = C$_{12}$-C$_{18}$ alkyl, and in particular lauryl, myristyl, palmityl, stearyl, oleyl or linoleyl

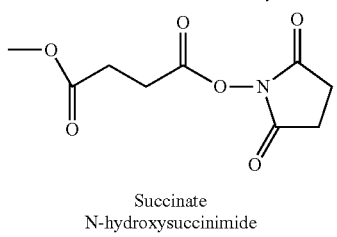

Succinate
N-hydroxysuccinimide or else chosen from —SO$_3$H, —COOH, —PO$_4$, —NR$_5$R$_6$, and —N$^+$R$_6$R$_6$R$_7$, wherein R$_5$, R$_6$ and R$_7$ are chosen, independent of one another, from H and from linear, branched and cyclic C$_1$-C$_{18}$ alkyls, such as methyl, optionally comprising at least one heteroatom and also carrying protective groups, such as t-butyloxycarbonyl (also known as BOC) and 9-fluorenylmethoxycarbonyl (also known as FmoC).

Mention may be made, among the $R_3$ radicals, for example, of the methyl, ethyl, propyl, benzyl, ethylhexyl, lauryl, stearyl, or behenyl ($-(CH_2)_{21}-CH_3$) chains and also fluorinated alkyl chains, such as, for example, heptadecafluorooctylsulphonylaminoethyl $CF_3-(CF_2)_7-SO_2-N(C_2H_5)-CH_2-CH_2$; or $-CH_2-CH_2-CN$, succinimido, maleimido, mesityl, tosyl, triethoxysilyl or phthalimido chains.

The amine units of the monomer may optionally be neutralized.

Mention may be made, among the salts, for example, of the salts of inorganic acids, such as sulphuric acid, hydrochloric acid, hydrobromic acid, hydriodic acid, phosphoric acid or boric acid. Mention may also be made, for example, of the salts of organic acids, which optionally comprise at least one carboxylic, sulphonic or phosphoric acid group. They may be linear, branched or cyclic aliphatic acids or aromatic acids. These acids may additionally comprise at least one heteroatom chosen from O and N, for example in the form of hydroxyl groups. Mention may, for example, be made of propionic acid, acetic acid, terephthalic acid, citric acid, and tartaric acid.

The acid groups may be neutralized with an inorganic base, such as LiOH, NaOH, KOH, Ca(OH)$_2$, NH$_4$OH, Mg(OH)$_2$ or Zn(OH)$_2$; or with an organic base, such as a primary, secondary or tertiary alkylamine, for example triethylamine or butylamine. This primary, secondary or tertiary alkylamine may comprise at least one nitrogen and/or oxygen atom and may thus comprise, for example, at least one alcohol functional group; mention may, for example, be made of 2-amino-2-methylpropanol, triethanolamine and 2-(dimethylamino)propanol. Mention may also be made, for example, of lysine or 3-(dimethylamino)propylamine.

Mention may be made, among the monomers of formula (I) of:
  polyethylene glycol (meth)acrylate, wherein $R_1$ is chosen from H and methyl, Z is COO, x=1, m=0, and $R_3$=H;
  methylpolyethylene glycol (meth)acrylate, also known as methoxypolyethylene glycol (meth)acrylate, wherein $R_1$ is chosen from H and methyl, Z is COO, x=1, m=0, and $R_3$=methyl;
  alkylpolyethylene glycol (meth)acrylates, wherein $R_1$ is chosen from H or methyl, Z is COO, x=1, m=0, and $R_3$=alkyl;
  phenylpolyethylene glycol (meth)acrylate, also known as polyethylene glycol phenyl ether (meth)acrylate, wherein $R_1$ is chosen from H and methyl, Z is COO, x=1, m=0, and $R_3$=phenyl;
  the following monomer:

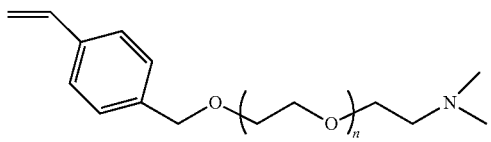

wherein n ranges from 3 to 100 inclusive, such as from 5 to 50 inclusive, for example, from 7 to 30 inclusive.

Examples of commercial monomers are:
  CD 350 (methoxypolyethylene glycol 350 methacrylate) and CD 550 (methoxypolyethylene glycol 550 methacrylate), supplied by Sartomer Chemicals;
  M90G (methoxypolyethylene glycol (9 repeat units) methacrylate) and M230G (methoxypolyethylene glycol (23 repeat units) methacrylate), available from Shin-Nakamura Chemicals;
  methoxypolyethylene glycol methacrylates with mean molecular weights of 300, 475, or 1100, available from Sigma-Aldrich;
  methoxypolyethylene glycol acrylate with a mean molecular weight of 426, available from Sigma-Aldrich;
  methoxypolyethylene glycol methacrylates, available from Laporte under the trade names: MPEG 350, MPEG 550, S10W, and S20W;
  polyethylene glycol monomethyl ether, mono(succinimidyl succinate) ester, products with a mean molecular weight of 1900 or 5000, from Polysciences;
  behenylpolyethylene glycol PEG-25 methacrylate, available from Rhodia under the name Sipomer BEM;
  polyethylene glycol phenyl ether acrylates with mean molecular weights of 236, 280, or 324, available from Aldrich;
  methoxypolyethylene glycol 5000 2-(vinylsulphonyl) ethyl ether, available commercially from Fluka;
  polyethylene glycol ethyl ether methacrylate, available from Aldrich; and
  polyethylene glycol 8000, 4000, and 2000 methacrylates, from Monomer-Polymer & Dajac Laboratories.

The at least one monomer of formula (I), alone or as a mixture, is present in an amount ranging from 10% to 80% by weight, relative to the total weight of the copolymer, such as from 20% to 70% by weight, for example, from 30% to 60% by weight, relative to the total weight of the copolymer.

The ethylenic copolymer according to the present disclosure also comprises at least one anionic monomer, and salts thereof, chosen from maleic anhydride and monomers of formula (II).

As used herein, the term "anionic monomer" refers to a monomer, which may carry a negative charge ranging from pH 4 to pH 12.

The monomers may thus be of formula:

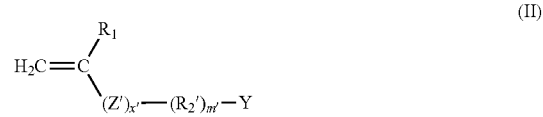

(II)

wherein:
  $R_1$ is chosen from a hydrogen atom and linear and branched hydrocarbon radicals $C_pH_{2p+1}$ wherein p is an integer between 1 and 12 inclusive; in at least one embodiment, for example, $R_1$ is chosen from methyl, ethyl, propyl, and butyl radicals. In another embodiment, $R_1$ is chosen from hydrogen and a methyl radical.
  Z' is a divalent group chosen from $-COO-$, $-OCO-$ and $-O-$, $-SO_2-$, $-CO-O-CO-$, and $-CO-CH_2-CO-$; in at least one embodiment, Z' is $-COO-$;
  x' is chosen from 0 or 1, for example 1;
  $R_2'$ is chosen from linear, branched and cyclic, saturated and unsaturated, optionally aromatic, divalent hydrocarbon radicals having from 1 to 30 carbon atoms which may comprise from 1 to 18 heteroatoms chosen from O, N, S, F, Si, and P; in the $R_2'$ radical, the heteroatom or heteroatoms, when they are present, may be inserted into the chain of the $R_2'$ radical or the $R_2'$ radical may be substituted by at least one group comprising them, such as hydroxyl.

For example, in at least one embodiment, $R_2'$ comprises:

an alkylene radical, such as methylene, ethylenic, propylene, n-butylene, isobutylene, tert-butylene, n-hexylene, n-octylene, n-dodecylene, n-octadecylene, n-tetradecylene or n-docosenylene;

a phenylene radical —$C_6H_4$— (ortho, meta or para) optionally substituted by a $C_1$-$C_{12}$ alkyl radical optionally comprising from 1 to 25 heteroatoms chosen from N, O, S, F, Si and/or P; or a benzylene radical —$C_6H_4$—$CH_2$— optionally substituted by a $C_1$-$C_{12}$ alkyl radical optionally comprising from 1 to 25 heteroatoms chosen from O, N, S, F, Si, and P;

a radical of formula —$CH_2$—O—CO—O—, —$CH_2$—$CH_2$—O—CO—O—, —$CH_2$—CO—O—, —$CH_2$—O—CO—NH—, —$CH_2$—$CH_2$—O—CO—NH—, —$CH_2$—NH—CO—NH—, —$CH_2$—$CH_2$—NH—CO—NH—, —$CH_2$—CHOH—, —$CH_2$—$CH_2$—CHOH—, —$CH_2$—$CH_2$—CH—O—, and —$CH_2$—$CH_2$—CHR'—O— wherein R' is chosen from a linear and branched $C_1$-$C_{22}$ alkyl radicals optionally comprising from 1 to 12 heteroatoms chosen from O, N, S, F, Si and P; and mixtures thereof.

m' is chosen from 0 and 1;

Y is a group chosen from —COOH, —$SO_3H$, —$OSO_3H$, —$PO_3H_2$, and —$OPO_3H_2$.

The acid groups may be neutralized with an inorganic or organic base as indicated above.

It is understood that, according to the state of the art, the $SO_4H$ and $PO_4H_2$ groups are bonded to $R_2'$ via the oxygen atom, whereas the $SO_3H$ and $PO_3H_2$ groups are bonded to $R_2'$ via the S and P atoms respectively.

Mention may be made, among the anionic monomers useful herein, for example, of maleic anhydride, acrylic acid, methacrylic acid, crotonic acid, itaconic acid, fumaric acid, maleic acid, 2-carboxyethyl acrylate ($CH_2$=CH—C(O)—O—($CH_2$)$_2$—COOH), styrenesulphonic acid, vinylbenzoic acid, vinylphosphonic acid, sulphopropyl (meth)acrylate, sulphatoethyl (meth)acrylate, and salts thereof, such as the ammonium salts.

The at least one anionic monomer, alone or as a mixture, is present in the composition of the present disclosure in an amount ranging from 20% to 90% by weight, relative to the total weight of the copolymer, such as from 30% to 80% by weight, and for example, from 40% to 70% by weight, relative to the total weight of the copolymer.

The ethylenic copolymer according to the present disclosure may optionally comprise other additional monomers than those mentioned above. When it comprises such other additional monomers, the latter are necessarily chosen from nonionic monomers, which are to be hydrophilic within the meaning of the present disclosure.

As used herein, the term "hydrophilic monomer" refers to monomers having a value of the logarithm of the 1-octanol/water apparent partition coefficient, also referred to as log P, of less than or equal to 2, for example from −8 to 2, such as less than or equal to 1.5, for example, less than or equal to 1, and further for example, from −7 to 1, such as from −6 to 0.

The log P values are known and may be determined according to a standard test, which determines the concentration of the monomer in the octanol and the water.

The values may, for example, be calculated using the ACD (Advanced Chemistry Development) Software Solaris V4.67 software; they may also be obtained from Exploring QSAR: hydrophobic, electronic and steric constants (ACS professional reference book, 1995).

There also exists an Internet site, which provides estimated values (address: http://esc.syrres.com/interkow/kowdemo.htm).

The log P values for some standard monomers, determined using the ACD software, are shown below:

| | Methacrylate (* or methacrylamide) | Acrylate (* or acrylamide) |
|---|---|---|
| Methyl (meth)acrylate | 1.346 ± 0.250 | 0.793 ± 0.223 |
| Ethyl (meth)acrylate | 1.877 ± 0.250 | 1.325 ± 0.223 |
| Propyl (meth)acrylate | 2.408 ± 0.250 | 1.856 ± 0.223 |
| Isopropyl (meth)acrylate | 2.224 ± 0.254 | 1.672 ± 0.228 |
| Butyl (meth)acrylate | 2.940 ± 0.250 | 2.387 ± 0.223 |
| Isobutyl (meth)acrylate | 2.756 ± 0.254 | 2.208 ± 0.228 |
| tert-Butyl (meth)acrylate | 2.574 ± 0.261 | 2.022 ± 0.238 |
| Cyclohexyl (meth)acrylate | 3.405 ± 0.252 | 2.853 ± 0.226 |
| Octyl (meth)acrylate | 5.065 ± 0.521 | 4.513 ± 0.224 |
| Lauryl (meth)acrylate | 7.190 ± 0.251 | 6.638 ± 0.224 |
| Tridecyl (meth)acrylate | 7.712 ± 0.251 | 7.170 ± 0.224 |
| Cetyl (meth)acrylate | 9.316 ± 0.251 | 8.764 ± 0.224 |
| Palmityl (meth)acrylate | >9 | >9 |
| Stearyl (meth)acrylate | 10.379 ± 0.251 | 9.826 ± 0.224 |
| Behenyl (meth)acrylate | 11.952 ± 0.225 | 12.504 ± 0.251 |
| Oleyl (meth)acrylate | >9 | 9.308 ± 0.232 |
| Tetrahydrofurfuryl (meth)acrylate | 1.352 ± 0.283 | 0.800 ± 0.263 |
| 2-Ethylhexyl (meth)acrylate | 4.881 ± 0.254 | 4.329 ± 0.229 |
| 2-Hydroxyethyl (meth)acrylate | 0.718 ± 0.277 | 0.166 ± 0.258 |
| Ethoxyethyl (meth)acrylate | 1.887 ± 0.293 | 1.335 ± 0.268 |
| Hydroxypropyl (meth)acrylate | | 0.383 ± 0.241 |
| N-Isopropyl(meth)acrylamide* | 0.748 ± 0.276 | 0.195 ± 0.256 |
| N-Octyl(meth)acrylamide* | 3.558 ± 0.273 | 3.036 ± 0.253 |
| N,N-Dimethyl(meth)acrylamide* | 0.906 ± 0.553 | −0.168 ± 0.556 |
| N,N-Dibutyl(meth)acrylamide* | 3.573 ± 0.570 | 3.021 ± 0.557 |
| Vinyl acetate | 0.730 ± 0.286 | |
| Methyl vinyl ether | 0.509 ± 0.286 | |
| Ethyl vinyl ether | 1.040 ± 0.286 | |
| Vinylcaprolactam | 1.499 ± 0.207 | |
| Vinylpyrrolidone | 0.370 ± 0.206 | |
| N-Vinylacetamide | 0 ± 0.231 | |

The additional hydrophilic monomers may, for example, be chosen from those of formula (III), alone or as a mixture:

(III)

wherein:

$R'_1$ is chosen from hydrogen and —$CH_3$;

Z" is a divalent group chosen from —COO—, —CONH—, —$CONCH_3$—, —OCO—, —$SO_2$—, —CO—O—CO—, —CO—$CH_2$—CO— and —O—; in at least one embodiment, for example, Z is chosen from —COO— and —CONH—;

x" is chosen from 0 and 1;

R" is chosen from linear, branched and cyclic, saturated and unsaturated, optionally aromatic, hydrocarbon radicals having from 1 to 30 carbon atoms, which optionally comprise from 1 to 18 heteroatoms chosen from O, N, S, F, Si, and P.

In the R" radical, the heteroatom or heteroatoms, when they are present, may be inserted into the chain of the radical or the radical may be substituted by at least one group comprising them, such as hydroxyl, ester, amide, urethane or urea. For example, R" may chosen from methyl, ethyl, propyl, isopropyl, n-butyl, isobutyl, tert-butyl, phenyl, benzyl and furfuryl radicals and radicals of formula —$CH_2$—$CH_2$—$CH_2OH$, —$CH_2$—$CH_2$—OH and —$CH_2$—$CH_2$—$CH_2$—OH.

The at least one additional nonionic hydrophilic monomer is chosen, for example, from the following monomers: methyl methacrylate, methyl acrylate, ethyl methacrylate, ethyl acrylate, propyl acrylate, isopropyl acrylate, tetrahydrofurfuryl methacrylate, tetrahydrofurfuryl acrylate, 2-hydroxyethyl methacrylate, 2-hydroxyethyl acrylate, ethoxyethyl methacrylate, ethoxyethyl acrylate, N-isopropylacrylamide, N-isopropylmethacrylamide, N,N-dimethylacrylamide, N,N-dimethylmethacrylamide, vinyl acetate, methyl vinyl ether, ethyl vinyl ether, vinylpyrrolidone, N-vinylcaprolactam, N-vinylacetamide, hydroxypropyl acrylate, N-vinyllactam, acrylamide, N-methylacrylamide, N,N-dimethylacrylamide, N-methyl-N-vinylacetamide, N-vinylformamide, N-methyl-N-vinylformamide, and vinyl alcohol (copolymerized in the vinyl acetate form and then hydrolyzed).

The at least one additional nonionic hydrophilic monomer, alone or as a mixture, may not be present in the copolymer according to the disclosure (e.g., 0% by weight) or else may be present in an amount ranging up to 70% by weight, relative to the total weight of the copolymer; for example, it may be present in an amount ranging from 0.1% to 35% by weight, such as from 1% to 25% by weight, for example of 3 to 15% by weight, and further for example, from 5% to 9.5% by weight, relative to the total weight of the copolymer.

The copolymer is, for example, a polymer comprising an overall negative charge, although it may comprise possible amine units.

The copolymers according to the disclosure may be prepared according to standard conventional radical polymerization methods well known to those skilled in the art and as described, for example, in the work "Chimie et physico-chimie des polymères" [Chemistry and Physical Chemistry of Polymers]", by Gnanou et al. (published by Dunod).

For example, these copolymers may be prepared by:
  direct polymerization in solution in water, with or without preneutralization of the anionic unit;
  polymerization as an emulsion in water, with or without preneutralization of the anionic unit and with use of a surfactant; and/or
  polymerization in an organic solvent, such as ethanol or methyl ethyl ketone, with or without preneutralization of the anionic unit, followed by a stage of dissolving or dispersing in water with evaporation of the solvent.

These polymerizations may be carried out in the presence of a radical initiator, for example, of peroxide type (Trigonox 21S: tert-butyl peroxy-2-ethylhexanoate) or azo type (AIBN V50: 2,2'-azobis(2-amidinopropane) dihydrochloride), which may be present in an amount ranging from 0.3% to 5% by weight, relative to the total weight of the copolymer.

The copolymers according to the disclosure are non-crosslinked. They are provided in the form of random ethylenic copolymers, which are, for example, film-forming, of at least one ethylenic monomer comprising PEG groups (the PEG groups may be pendent along the backbone) and of at least one ethylenic monomer comprising anionic functional groups and optionally at least one other monovalent nonionic hydrophilic ethylenic comonomer.

As used herein, the term "ethylenic polymer" refers to a polymer obtained by polymerization of monomers comprising an ethylenic unsaturation.

As used herein, the term "'film-forming' polymer" refers to a polymer capable of forming, by itself alone or in the presence of an additional agent which is able to form a film, a continuous and adherent film on a support, such as on keratinous substances.

The copolymers of the present disclosure exhibit a weight-average molecular mass (Mw) which ranges, for example, from 500 and 5,000,000, such as from 1000 to 3,000,000 and further for example, from 2000 to 2,000,000, such as from 4000 to 500,000, inter alia, from 7000 to 250,000, such as from 8000 to 100,000.

The weight-average molar masses (Mw) may be determined by gel permeation chromatography or by light scattering, according to how accessible the method is, e.g., considering the solubility of the polymers.

The polymers according to the present disclosure may, for example, be conveyed in an aqueous medium, that is to say that they are water-soluble or water-dispersible.

Dissolving or dispersing in water may be carried out by direct dissolution of the polymer, if it is soluble, or else by neutralization of the acid units, so as to render the polymer soluble or dispersible in water.

Dissolving, or dispersing in an aqueous medium may also be carried out via an intermediate stage of dissolution in an organic solvent, followed by the addition of water, before evaporation of the organic solvent.

Furthermore, the polymers according to the present disclosure, for example, may exhibit a viscosity in water which is suitable for the applications envisaged and which may be, for example, range from 1 mPa·s to 1000 mPa·s, such as from 1.5 mPa·s to 750 mPa·s and further for example, from 2 mPa·s to 500 mPa·s.

The viscosity may be measured using a Brookfield viscometer for a 15% by weight solution of polymer in water or methyl ethyl ketone (solvent chosen according to the solubility of the polymer and/or the polymerization method) at 25° C. with a rotor of spindle type chosen from the Brookfield models numbered 00 to 07, such as rotor No. 1, for a measuring time of 5 minutes, at a speed of between 0.1 and 6 revolutions/minute, for example, 6 revolutions/minute. The viscosity is measured after complete dissolution of the polymer in water or methyl ethyl ketone.

A person skilled in the art may choose the rotor on the basis of general knowledge known in the art. The speed may also chosen so as to be able to carry out the measurement within an acceptable range of accuracy for liquid compounds which are not very viscous.

In addition, the copolymers according to the disclosure, for example, exhibit a glass transition temperature (Tg) ranging from −150° C. to 20° C., such as from −120° C. to 10° C., further for example, from −100° C. to 0° C.; the Tg is measured according to the method given before the examples.

The polymers according to the disclosure may also, for example, exhibit a melting point (M.p.) ranging from −100° C. to 80° C., such as from −80° C. to 50° C., further for example, from −70° C. and 45° C., such as from −10° C. to 25° C.

In addition, the copolymers according to the disclosure, for example, exhibit a water uptake ranging from 3% to 150% by weight, such as from 4% to 120% by weight, further for example, from 4.5% to 90% by weight, at 75% relative humidity (75% RH); the water uptake may be measured according to the method given before the examples.

They may also exhibit a water uptake ranging from 5% to 90% by weight, such as from 7.5% to 75% by weight, further for example, from 15% to 60% by weight, at 85% relative humidity (85% RH).

The copolymers according to the disclosure may be used in the field of cosmetics. They may also be present in the composition in the dissolved form, for example dissolved in water or an organic solvent, or else in the form of an aqueous or organic dispersion.

They may be used in cosmetic or pharmaceutical compositions in an amount ranging from 0.01% to 50% by weight on a dry basis, such as from 0.1% to 30% by weight, for example, from 1% to 25% by weight, such as from 3% to 20% by weight, relative to the total weight of the copolymer.

The cosmetic or pharmaceutical compositions according to the disclosure comprise, in addition to the polymers, a physiologically acceptable medium, such as a cosmetically or dermatologically acceptable medium, that is to say a medium compatible with keratinous substances, such as the skin of the face or body, the hair, the eyelashes, the eyebrows, and the nails.

The composition may thus comprise a hydrophilic medium comprising water or a mixture of water and at least one hydrophilic organic solvent, such as alcohols and for example, linear or branched $C_1$-$C_6$ monoalcohols, such as ethanol, tert-butanol, n-butanol, isopropanol or n-propanol, and polyols, such as glycerol, diglycerol, propylene glycol, sorbitol, pentylene glycol and polyethylene glycols, or alternatively glycol ethers, such as $C_2$ glycol ethers, and $C_2$-$C_4$ aldehydes which are hydrophilic.

The water or the mixture of water and at least one hydrophilic organic solvent may be present in the composition according to the disclosure in an amount ranging from 0.1% to 99% by weight, relative to the total weight of the composition, and for example, from 10% to 80% by weight.

The composition can also comprise a fatty phase, composed, for example, of fatty substances which may be liquid at ambient temperature (25° C. in general) and/or of fatty substances, which are solid at ambient temperature, such as waxes, pasty fatty substances, gums and their mixtures. These fatty substances may be of animal, vegetable, mineral, or synthetic origin. This fatty phase may additionally comprise at least one lipophilic organic solvent.

Mention may be made, as fatty substances which are liquid at ambient temperature, often known as oils, which may be used in the disclosure, for example, of hydrocarbon oils of animal origin, such as perhydrosqualene; vegetable hydrocarbon oils, such as liquid triglycerides of fatty acids comprising 4 to 10 carbon atoms, such as triglycerides of heptanoic or octanoic acids, or sunflower, maize, soybean, grape seed, sesame, apricot, macadamia, castor or avocado oils, triglycerides of caprylic/capric acids, jojoba oil or shea butter oil; linear or branched hydrocarbons of mineral or synthetic origin, such as liquid paraffins and theft derivatives, liquid petrolatum, polydecenes or hydrogenated polyisobutene, such as parleam; synthetic esters and ethers, for example, of fatty acids, such as, purcellin oil, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate or diethylene glycol diisononanoate; pentaerythritol esters; fatty alcohols having from 12 to 26 carbon atoms, such as octyldodecanol, 2-butyloctanol, 2-hexyldecanol, 2-undecylpentadecanol or oleyl alcohol; partially hydrocarbon-comprising and/or silicone-comprising fluorinated oils; silicone oils, such as volatile or nonvolatile and linear or cyclic polymethylsiloxanes (PDMS) which are liquid or pasty at ambient temperature, such as cyclomethicones, dimethicones, optionally comprising a phenyl group, such as phenyl trimethicones, phenyltrimethylsiloxydiphenylsiloxanes, diphenylmethyldimethyltrisiloxanes, diphenyl dimethicones, phenyl dimethicones or polymethylphenylsiloxanes; and mixtures thereof.

These oils may be present in an amount ranging from 0.01% to 90% by weight, and for example, from 0.1% to 85% by weight, relative to the total weight of the composition.

The composition according to the disclosure may also comprise at least one physiologically acceptable organic solvent.

These solvents may generally be present in an amount ranging from 0.1% to 90% by weight, such as from 0.5% to 85% by weight, for example from 10 to 80% by weight, relative to the total weight of the composition, and further for example, from 30% to 50% by weight.

Mention may, for example, be made, in addition to the hydrophilic organic solvents mentioned above, of ketones which are liquid at ambient temperature, such as methyl ethyl ketone, methyl isobutyl ketone, diisobutyl ketone, isophorone, cyclohexanone or acetone; propylene glycol ethers which are liquid at ambient temperature, such as propylene glycol monomethyl ether, propylene glycol monomethyl ether acetate or dipropylene glycol mono(n-butyl)ether; short-chain esters (having from 3 to 8 carbon atoms in total), such as ethyl acetate, methyl acetate, propyl acetate, n-butyl acetate or isopentyl acetate; ethers which are liquid at 25° C., such as diethyl ether, dimethyl ether or dichlorodiethyl ether; alkanes which are liquid at 25° C., such as decane, heptane, dodecane, isododecane or cyclohexane; cyclic aromatic compounds which are liquid at 25° C., such as toluene and xylene; and aldehydes which are liquid at 25° C., such as benzaldehyde or acetaldehyde, and their mixtures.

As used herein, the term "wax" within the meaning of the present disclosure refers to a lipophilic compound, solid at ambient temperature (25° C.), with a reversible solid/liquid change of state, having a melting point of greater than or equal to 25° C. which may range up to 120° C. On bringing the wax to the liquid state (melting), it is possible to render it miscible with the oils possibly present and to form a microscopically homogeneous mixture but, on bringing the temperature of the mixture back to ambient temperature, recrystallization of the wax from the oils of the mixture may be obtained. The melting point of the wax may be measured using a differential scanning calorimeter (DSC), for example the calorimeter sold under the name DSC 30 by Mettler.

The waxes may be hydrocarbon, fluorinated and/or silicone waxes and may be of vegetable, mineral, animal and/or synthetic origin. For example, the waxes exhibit a melting point of greater than 30° C., such as greater than 45° C. Mention may be made, as wax which may be used in the composition of the disclosure, for example, of beeswax, carnauba wax, candelilla wax, paraffin wax, microcrystalline waxes, ceresin or ozokerite; synthetic waxes, such as polyethylene or Fischer-Tropsch waxes, or silicone waxes, such as alkyl or alkoxy dimethicones having from 16 to 45 carbon atoms.

The gums may be generally high molecular weight polydimethylsiloxanes (PDMSs) or cellulose gums or polysaccharides and the pasty substances are generally hydrocarbon compounds, such as lanolins and their derivatives, or PDMSs.

The nature and the amount of the solid substances depend on the desired mechanical properties and the desired textures. By way of example, the composition may comprise from 0.1% to 50% by weight of waxes, relative to the total weight of the composition, and further for example, from 1 to 30% by weight.

The composition according to the disclosure may additionally comprise, in a particulate phase, pigments and/or pearlescent agents and/or fillers commonly used in cosmetic compositions.

The composition may also comprise other coloring materials chosen from water-soluble dyes or fat-soluble dyes well known to a person skilled in the art.

As used herein, the term "pigments" refers to white or colored and inorganic or organic particles of any shape which may be insoluble in the physiological medium and which may be intended to color the composition.

As used herein, the term "fillers" refers to colorless or white, inorganic or synthetic and lamellar or nonlamellar particles which may be intended to give body or stiffness to the composition and/or softness, mattness and uniformity to the makeup.

As used herein, the term "pearlescent agents" refers to iridescent particles of any shape produced such as by certain shellfish in their shells or else synthesized.

The pigments may be present in the composition in an amount ranging from 0.01% to 25% by weight, relative to the total weight of the composition and for example, ranging from 3% to 10% by weight. They may be white or colored and inorganic or organic. Mention may be made, for example, of titanium, zirconium or cerium oxides, zinc, iron or chromium oxides, ferric blue, chromium hydrate, carbon black, ultramarines (aluminosilicate polysulphides), manganese pyrophosphate and some metal powders, such as those of silver or of aluminium. Mention may also be made, for example, of D&C pigments and lakes, commonly employed to confer a makeup effect on the lips and skin, which are calcium, barium, aluminium, strontium, or zirconium salts.

The pearlescent agents may be present in the composition in an amount ranging from 0.01% to 20% by weight, such as ranging from 3% to 10% by weight, relative to the total weight of the composition. Mention may be made, among the pearlescent agents which may be envisaged, for example, of natural mother-of-pearl, mica covered with titanium oxide, with iron oxide, with natural pigment or with bismuth oxychloride, and coloured titanium oxide-coated mica.

Mention may be made, among fat-soluble or water-soluble dyes, which may be present in the composition, alone or as a mixture, in an amount ranging from 0.001% to 15% by weight, such as from 0.01% to 5% by weight and for example, from 0.1% to 2% by weight, relative to the total weight of the composition, for example, of the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll, methylene blue, cochineal carmine, haloacid, azo or anthraquinone dyes, copper sulphate, iron sulphate, Sudan brown, Sudan red and annatto, and sugarbeet juice and carotene.

The composition according to the disclosure may additionally comprise at least one filler, such as in an amount ranging from 0.01% to 50% by weight, relative to the total weight of the composition, for example, ranging from 0.02% to 30% by weight. The at least one filler may be inorganic or organic and of any shape, platelet, spherical or oblong. Mention may be made, for example, of talc, mica, silica, kaolin, polyamide (Nylon®) powders, poly(β-alanine) powders, polyethylene powders, tetrafluoroethylene polymer (Teflon®) powders, lauroyllysine, starch, boron nitride, polymeric, hollow microspheres, such as those of poly(vinylidene chloride)/acrylonitrile, for example Expancel® (Nobel Industrie), of acrylic acid copolymers (Polytrap® from Dow Corning) and silicone resin microbeads (Tospearls® from Toshiba, for example), particles of polyorganosiloxane elastomers, precipitated calcium carbonate, magnesium carbonate and basic magnesium carbonate, hydroxyapatite, hollow silica microspheres (Silica Beads® from Maprecos), glass or ceramic microcapsules, or metal soaps derived from organic carboxylic acids having from 8 to 22 carbon atoms, such as from 12 to 18 carbon atoms, for example zinc stearate, magnesium stearate, lithium stearate, zinc laurate or magnesium myristate.

The composition may furthermore comprise an additional polymer, such as a film-forming polymer. According to the present disclosure, the term "film-forming polymer" includes a polymer capable of forming, by itself alone or in the presence of an additional agent which is able to form a film, a continuous and adherent film on a support, such as on keratinous substances. Mention may be made, among the film-forming polymers capable of being used in the composition of the present disclosure, for example, of synthetic polymers of radical type or of polycondensate type, polymers of natural origin and mixtures thereof, such as acrylic polymers, polyurethanes, polyesters, polyamides, polyureas or cellulose polymers, such as nitrocellulose.

The composition may also comprise at least one surface-active agent, which is present in an amount ranging from 0.01% to 50% by weight, such as from 0.1% to 40% and further for example, from 0.5% to 30%, relative to the total weight of the composition.

The at least one surface-active agent may be chosen from anionic, amphoteric, nonionic and cationic surface-active agents, and mixtures thereof.

The at least one surfactant, i.e., the at least one surface-active agent, which is suitable for implementing the present disclosure are, for example, alone or as a mixture:

anionic surfactants, among which may be mentioned, alone or as mixtures, the salts (e.g., alkali metal, such as sodium, salts, ammonium salts, amine salts, aminoalcohol salts or magnesium salts) of the following compounds: alkyl sulfates, alkyl ether sulfates, alkylamido ether sulfates, alkylarylpolyether sulfates, monoglyceride sulfates; alkylsulfonates, alkyl phosphates, alkylamidesulfonates, alkylarylsulfonates, α-olefinsulfonates, paraffinsulfonates; alkyl sulfosuccinates, alkyl ether sulfosuccinates, alkylamidesulfosuccinates; alkyl sulfosuccinamates; alkyl sulfoacetates; alkyl ether phosphates; acylsarcosinates; acylisethionates and N-acyltaurates, the alkyl or acyl radical of all these different compounds, for example, comprising from 8 to 24 carbon atoms, and the aryl radical, for example, denoting a phenyl or benzyl group.

Mention may also be made, for example, of the salts of fatty acids, such as the salts of oleic, ricinoleic, palmitic and stearic acids, the acids of coconut oil or of hydrogenated coconut oil; acyllactylates wherein the acyl radical comprises from 8 to 20, carbon atoms; alkyl-D-galactosideuronic acids and their salts, as well as polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$) alkylamido ether carboxylic acids and their salts, for example, those comprising from 2 to 50 ethylenic oxide groups, and mixtures thereof.

nonionic surfactants, among which may be mentioned, alone or as mixtures, for example, polyethoxylated, polypropoxylated or polyglycerolated fatty alcohols, α-diols, alkylphenols or acids which have a fatty chain comprising, for example, from 8 to 18 carbon atoms, it being possible for the number of ethylenic oxide or propylene oxide groups to range such as from 2 to 50 and it being possible for the number of glycerol groups to range such as from 2 to 30.

Mention may also be made, for example, of the copolymers of ethylenic oxide and of propylene oxide and the condensates of ethylenic oxide and of propylene oxide with fatty alcohols; the polyethoxylated fatty amides such as having from 2 to 30 mol of ethylenic oxide; the polyglycerolated fatty amides on average comprising from 1 to 5 glycerol groups and for example, from 1.5 to 4; the oxyethylenated esters of sorbitan fatty adds having from 2 to 30 mol of ethylenic oxide; the sucrose esters of fatty acids, the polyethylene glycol esters of fatty acids, alkylpolyglycosides, the N-alkylglucamine derivatives, or amine oxides, such as the oxides of ($C_{10}$-$C_{14}$)alkylamines or the N-acylaminopropylmorpholine oxides.

amphoteric surfactants, among which may be mentioned, alone or as mixtures, derivatives, for example, of aliphatic secondary or tertiary amines wherein the aliphatic radical is a linear or branched chain comprising from 8 to 22 carbon atoms and comprising at least one water-solubilizing anionic group (for example, carboxylate, sulfonate, sulfate, phosphate or phosphonate); mention may also be made, for example, of ($C_8$-$C_{20}$)alkyl betaines, sulfobetaines, ($C_8$-$C_{20}$)alkyl amido($C_1$-$C_6$) alkyl betaines, such as cocoamidopropyl betaine, or ($C_8$-$C_{20}$)alkyl amido($C_1$-$C_6$)alkyl sulfobetaines.

cationic surfactants, among which may be mentioned, for example, alone or as mixtures, of:

A) the quaternary ammonium salts of the following general formula (XVI):

wherein X is an anion Chosen from halides (chloride, bromide or iodide) and ($C_2$-$C_6$)alkyl sulfates, such as methyl sulfate, phosphates, alkyl- or alkylarylsulfonates, and anions derived from an organic acid, such as acetate or lactate, and a) the $R_1$ to $R_3$ radicals, which may be identical or different, are chosen from linear and branched aliphatic radicals comprising from 1 to 4 carbon atoms and aromatic radicals, such as aryl or alkylaryl. The aliphatic radicals may comprise heteroatoms, such as, for example, oxygen, nitrogen, sulphur or halogens. The aliphatic radicals are, for example, chosen from alkyl, alkoxy and alkylamide radicals, $R_4$ is chosen from a linear and branched alkyl radical comprising from 16 to 30 carbon atoms.

For example, in at least one embodiment, the cationic surfactant is a behenyltrimethylammonium salt (e.g., chloride).

b) the $R_1$ and $R_2$ radicals, which may be identical or different, are chosen from linear and branched aliphatic radicals comprising from 1 to 4 carbon atoms and aromatic radicals, such as aryl or alkylaryl. The aliphatic radicals may comprise heteroatoms, such as, oxygen, nitrogen, sulphur or halogens. The aliphatic radicals are, for example, chosen from alkyl, alkoxy, alkylamide and hydroxyalkyl radicals comprising approximately from 1 to 4 carbon atoms;

$R_3$ and $R_4$, which may identical or different, are chosen from linear and branched alkyl radicals comprising from 12 to 30 carbon atoms, the radical comprising at least one ester or amide functional group.

$R_3$ and $R_4$ are chosen, for example, from ($C_{12}$-$C_{22}$)alkylamido($C_2$-$C_6$)alkyl and ($C_{12}$-$C_{22}$) alkyl acetate radicals.

For example, the cationic surfactant is a stearamidopropyldimethyl(myristyl acetate)ammonium salt (e.g. chloride).

B) imidazolinium quaternary ammonium salts, such as, for example, that of following formula (XVII):

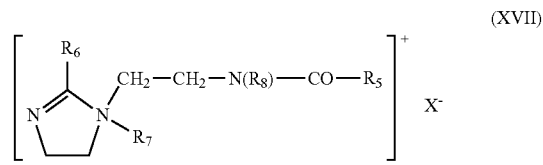

wherein
$R_5$ is chosen from alkenyl and alkyl radicals comprising from 8 to 30 carbon atoms, for example derivatives of tallow fatty acids;
$R_6$ is chosen from a hydrogen atom, $C_1$-$C_4$ alkyl radicals and alkenyl and alkyl radicals comprising from 8 to 30 carbon atoms;
$R_7$ is chosen from $C_1$-$C_4$ alkyl radicals;
$R_8$ is chosen from a hydrogen atom and $C_1$-$C_4$ alkyl radicals; and
X is an anion chosen from the group of the halides, phosphates, acetates, lactates, alkyl sulfates, and alkyl- and alkylarylsulfonates.
$R_5$ and $R_6$, in at least one embodiment, are chosen from a mixture of alkenyl and alkyl radicals comprising from 12 to 21 carbon atoms, such as derivatives of tallow fatty acids;
$R_7$, for example, comprises methyl; and $R_8$, for example, comprises hydrogen. Such a product is, for example, Quaternium-27 (CTFA 1997) or Quaternium-83 (CTFA 1997), which are sold under the names "REWOQUAT" W 75, W90, W75PG or W75HPG by Witco, C) di(quaternary ammonium) salts of formula (XVIII):

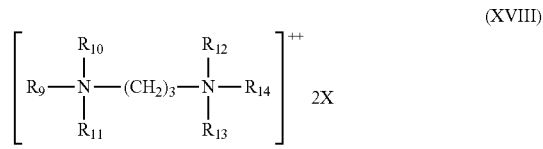

wherein $R_9$ is chosen from an aliphatic radical comprising approximately from 16 to 30 carbon atoms, $R_{10}$, $R_{11}$, $R_{12}$, $R_{13}$ and $R_{14}$, which may be identical or different, are chosen from hydrogen or alkyl radicals comprising from 1 to 4 carbon atoms, and X is an anion chosen from the group of the halides, acetates, phosphates, nitrates and methyl sulfates. Such di(quaternary ammonium) salts comprise, for example, propanetallowediammonium dichloride, D) quaternary ammonium salts comprising at least one ester functional group of following formula (XIX):

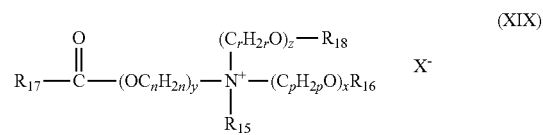

wherein:

$R_{15}$ is chosen from $C_1$-$C_6$ alkyl radicals and $C_1$-$C_6$ hydroxyalkyl and dihydroxyalkyl radicals;

$R_{16}$ is chosen from:

a

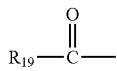

radical saturated and unsaturated, linear and branched, $C_1$-$C_{22}$ hydrocarbon radicals $R_{20}$, and a hydrogen atom, $R_{18}$ is chosen from:

a

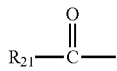

radical saturated and unsaturated, linear and branched, $C_1$-$C_6$ hydrocarbon radicals $R_{22}$, and a hydrogen atom, $R_{17}$, $R_{19}$ and $R_{21}$, which may be identical or different, are chosen from saturated and unsaturated, linear and branched, $C_7$-$C_{22}$ hydrocarbon radicals;

n, p and r, which may be identical or different, are integers having values ranging from 2 to 6;

y is an integer having a value ranging from 1 to 10;

x and z, which may be identical or different, are integers having values ranging from 0 to 10;

$X^-$ is chosen from an organic and inorganic, simple and complex anion; with the proviso that the sum x+y+z has a value ranging from 1 to 15, wherein when x has a value of 0, then $R_{16}$ denotes $R_{20}$, and when z has a value of 0, then $R_{18}$ denotes $R_{22}$.

The composition according to the disclosure may also comprise ingredients commonly used in cosmetics, such as vitamins, fragrances, pearlescent agents, thickeners, gelling agents, trace elements, softening agents, sequestering agents, basifying or acidifying agents, preservatives, sunscreens, antioxidants, agents for combating hair loss, antidandruff agents, propellants, ceramides or their mixtures. Of course, a person skilled in the art will take to choose this or these optional additional compounds and/or their amounts so that the desirable properties of the composition according to the disclosure are not, or not substantially, detrimentally affected by the envisaged addition.

In another embodiment, the composition according to the disclosure comprises at least one preservative; as used herein, the term "preservative" refers to any natural or artificial technological additive which has the aim of preserving the cosmetic composition from any detrimental physicochemical and microbial change. Mention may thus be made, for example, of:

antimicrobial preservatives: parabens or esters of 4-hydroxybenzoic acid, sorbic acid, 2-phenoxyethanol, formaldehyde, triclosan or quaternary ammoniums, and antioxidizing preservatives: tocopherol or vitamin E, essential oils, ascorbyl palmitate, BHT, BHA or gallates.

The composition according to the disclosure may be provided in the form of a suspension, a dispersion, such as oil in water, by virtue of vesicles; an optionally thickened, such as gelled, oily solution; an oil-in-water, water-in-oil or multiple emulsion; a gel or a foam; an oily or emulsified gel; a dispersion of vesicles, such as lipid vesicles; a two-phase or multiphase lotion; or a spray. This composition may have the appearance of a lotion, of a cream, of an ointment, of a soft paste, of a salve, of a cast or molded solid, such as cast or molded as a stick or in a dish, or of a compacted solid.

A person skilled in the art may choose the appropriate dosage form, and its method of preparation, on the basis of general knowledge known in the art, taking into account, on the one hand, the nature of the constituents used, such as their solubility in the vehicle, and, on the other hand, the application envisaged for the composition.

The cosmetic composition according to the disclosure may be provided in the form of a product for caring for and/or making up the skin of the body or face, the lips and the hair, of an antisun or self-tanning product, or indeed of a hair product.

For example, the present disclosure may be applicable in the hair field, such as for the form retention of the hairstyle or the shaping of the hair. The hair compositions are, for example, shampoos, gels, hair setting lotions, blow-drying lotions, or fixing and styling compositions, such as lacquers or sprays. The lotions may be packaged in various forms, such as in vaporizers, pump-action sprays or aerosol containers, in order to provide for application of the composition in the vaporized form or in the foam form.

In another embodiment, the compositions in accordance with the disclosure may be used for washing or treating keratinous substances, such as the hair, skin, eyelashes, eyebrows, nails, lips or scalp and for example, the hair.

The compositions according to the disclosure may be detergent compositions, such as shampoos, shower gels and foam baths. In this embodiment of the disclosure, the compositions comprise at least one washing base, generally an aqueous washing base.

The present disclosure further relates to a method for treating, such as for making up or caring for, keratinous substances, for example, the skin of the body or face, the nails, the hair, including body hair, and/or the eyelashes, comprising applying, to the keratinous substances, a cosmetic composition as defined above.

The application may optionally be followed by rinsing with water. Thus, this method according to the disclosure makes possible the form retention of the hairstyle or the treatment, care or washing of or removal of makeup from the skin, hair or any other keratinous substance.

The compositions of the disclosure may be further provided in the form of a rinse-out or leave-in conditioner; a perming, hair straightening, dyeing or bleaching compositions; or in the form of rinse-out compositions, to be applied before or after a dyeing, a bleaching, a perming or a hair straightening or between the two stages of a perming or of a hair straightening.

When the composition is provided in the form of a conditioner optionally to be rinsed out, it may, for example, comprises at least one cationic surfactant, such as in a concentration in an amount ranging from 0.1% to 10% by weight and for example, from 0.5% to 5% by weight, relative to the total weight of the composition.

The compositions of the disclosure may also be provided in the form of washing composition for the skin and for example, in the form of solutions or gels for the bath or shower or of makeup removers.

The compositions according to the disclosure may also be provided in the form of aqueous or aqueous/alcoholic lotions for caring for the skin and/or hair.

The present disclosure is illustrated in more detail in the following examples.

Other than in the examples, or where otherwise indicated, all numbers expressing quantities of ingredients, reaction conditions, and so forth used in the specification and claims are to be understood as being modified in alt instance by the term "about." Accordingly, unless indicated to the contrary, the numerical parameters set forth in the following specification and attached claims are approximations that may vary depending upon desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contain certain errors necessarily resulting from the standard deviation found in their respective testing measurements.

The following examples are intended to illustrate the present disclosure without limiting the scope as a result.

Measurement of the Tg

A film was prepared from a 6% by weight aqueous solution of polymer and was dried for 48 hours in a controlled atmosphere at 50% relative humidity and 25° C. The films thus obtained had a thickness ranging from 10 µm to 20 µm.

The measuring device is a DSC (TA Instruments).

The sample resulting from the film is placed in a sealed crucible and is heated according to the following protocol:
equilibrium at the starting temperature Ti;
heating 1: increase in the temperature at a rate of +10° C./min up to the final temperature Tf (° C.);
isotherm lasting 1 minute;
reduction in the temperature at a rate of −10° C./min down to Ti (° C.);
heating 2: increase in the temperature at a rate of +10° C./min up to Tf (° C.);
isotherm lasting 1 minute;
with Ti: Initial temperature −120° C.
with Tf: Final temperature +120° C.
The Tg values are measured during heating stages 1 and 2.

Measurement of the Water Uptake

Approximately 1 g of dry copolymer is placed in an aluminium dish with a diameter of 4.5 cm (0.01 m$^2$) tared beforehand T. Drying is allowed to take place in an oven at 60° C. under reduced pressure for 48 hours. The dishes are removed and are immediately weighed (e.g., less than one minute after being removed from the oven). P1 is obtained.

The dishes are subsequently placed in a glove box having the relative humidity under consideration (e.g., 75% RH or 85% RH) and are left therein for 6 hours. They are subsequently weighed again immediately after being removed from the glove box. P2 is obtained.

The water uptake is calculated in the following way: [(P2−P1)×100]/(P1−T)

EXAMPLE 1

50 ml of methyl ethyl ketone (MEK) were introduced into a (four-necked) reactor equipped with two dropping funnels, a reflux condenser and a mechanical stirrer and the reactor was brought to 80° C., At the same time, a solution 1 comprising 50 g of polyethylene glycol methacrylate (PEGM 550), 1 g of Trigonox 21S and 75 g of MEK was prepared.

A solution 2 comprising 75 ml of MEK and 50 g of acrylic acid was also prepared.

Solutions 1 and 2 were run into the four-necked reactor simultaneously over 30 minutes. The resulting solution was subsequently maintained at 80° C. for 5 hours. The orange-yellow solution obtained was cooled. 690 ml of 1N sodium hydroxide solution were then added with stirring and then the solvent (MEK) was evaporated. 95 g of copolymer were obtained.

EXAMPLE 2

In a way similar to Example 1, 50 g of polyethylene glycol methacrylate (PEGM 2000) and 50 g of ammonium sulphatoethyl methacrylate were reacted in 200 ml of water in the presence of 2.5 g of potassium persulphate. This mixture was heated at 70° C. for 4 hours and was then cooled to 25° C. An orange-coloured viscous solution was obtained with a polymer content of 33% on a dry basis.

EXAMPLE 3

In a way similar to Example 1, 75 g of polyethylene glycol methacrylate (PEGM 2000) and 25 g of 3-sulphopropyl acrylate, potassium salt, were reacted in 200 ml of water in the presence of 2.5 g of potassium persulphate. This mixture was heated at 70° C. for 4 hours and was then cooled to 25° C. A pale yellow solution was obtained with a polymer content of 30% on a dry basis.

EXAMPLE 4

In a similar way to Example 1, 75 g of polyethylene glycol methacrylate (PEGM 2000) and 25 g of ammonium sulphatoethyl methacrylate were reacted in 200 ml of water in the presence of 2.5 g of potassium persulphate. This mixture was heated at 70° C. for 4 hours and was then cooled to 25° C. A pale yellow solution was obtained with a polymer content of 33% on a dry basis.

EXAMPLE 5

The water uptakes, at 75% RH and the viscosities (Brookfield viscometer, speed 6 rev/min, 15% by weight solution of polymer in water, at 25° C., with a rotor of Brookfield No. 1 spindle type, measurement time: 5 minutes) of the polymers prepared above were measured.

The results are given in the table below:

| | Composition of the polymer (% by weight) | Solubility* | Water uptake | Viscosity at 15% |
|---|---|---|---|---|
| Example 1 | PEGM 550 50% Acrylic acid 50% NaOH neutralized 100% | Yes | 33% | 4 mPa · s |
| Example 2 | PEGM 550 50% Sulphatoethyl methacrylate, ammonium salt, 50% | Yes | 73% | 333 mPa · s |
| Example 3 | PEGM 2000 75% 3-Sulphopropyl | Yes | 80% | 21 mPa · s |

-continued

| | Composition of the polymer (% by weight) | Solubility* | Water uptake | Viscosity at 15% |
|---|---|---|---|---|
| Example 4 | acrylate, potassium salt, 25% PEGM 2000 75% Sulphatoethyl methacrylate, ammonium salt, 25% | Yes | 90% | 12.1 mPa·s |

*"Yes" means that the polymer was soluble in water at least up to 50% by weight.

EXAMPLE 6

A styling product composition was prepared comprising the following constituents (% by weight):
  6% of the polymer described in Example 4 (with a content of 33% on a dry basis),
  preservative, q.s.,
  water, q.s. for 100%.
The styling product composition obtained contributes a good styling effect with easy removal on shampooing.

EXAMPLE 7

A shampoo composition was prepared which comprises the following constituents (% by weight):
  7.5% of lauryl ether sulphate,
  2.5% of cocobetaine amphoteric surfactant (Dehyton AB30 from Cognis),
  5% of cocopolyglucoside surfactant (Plantacare 818 UP from Cognis),
  3% of the polymer described in Example 2 (with a content of 33% on a dry basis),
  water, q.s. for 100%.
Good disentangling properties and improved styling were found, in wet and dry surroundings.

What is claimed is:

1. A method for treating hair which comprises applying to the hair, a cosmetic composition comprising, in a physiologically acceptable medium, at least one random ethylenic copolymer consisting of:
  a) from 10% to 80% by weight, relative to the total weight of the copolymer, of at least one monomer chosen from compounds of formula (I):

$$H_2N=C\begin{array}{c}R_1\\ \diagdown\\ (Z)_x-(R_2)_m-(CH_2CH_2O)_n-R_3\end{array} \quad (I)$$

wherein:
    $R_1$ is chosen from a hydrogen atom and linear and branched hydrocarbon radicals $C_pH_{2p+1}$ wherein p is an integer ranging from 1 to 12 inclusive;
    Z is a divalent group chosen from —COO—, —CONH—, —CONCH$_3$—, —OCO—, —O—, —SO$_2$—, —CO—O—CO— and —CO—CH$_2$—CO—;
    x is chosen from 0 and 1;
    $R_2$ is chosen from linear, branched and cyclic, saturated and unsaturated, optionally aromatic, divalent hydrocarbon radicals having from 1 to 30 carbon atoms, m is chosen from 0 and 1;
    n is an integer ranging from 3 to 300 inclusive;
    $R_3$ is chosen from a hydrogen atom and linear, branched and cyclic, saturated and unsaturated, optionally aromatic, hydrocarbon radical with 1 to 30 carbon atoms; and salts thereof; and
  b) from 20% to 90% by weight, relative to the total weight of the copolymer, of an anionic monomer, chosen from monomers of formula (II):

$$H_2C=C\begin{array}{c}R_1\\ \diagdown\\ (Z')_{x'}-(R_2')_{m'}-Y\end{array} \quad (II)$$

wherein:
    $R_1$ is chosen from a hydrogen atom and linear and branched hydrocarbon radicals $C_pH_{2p+1}$ wherein p is an integer ranging from 1 to 12 inclusive;
    Z' is a divalent group chosen from —COO—, —OCO— or —O—, —SO$_2$—, —CO—O—CO— and —CO—CH$_2$—CO—;
    x' is chosen from 0 and 1;
    $R'_2$ is chosen from linear, branched and cyclic, saturated and unsaturated, optionally aromatic, divalent hydrocarbon radicals having 1 to 30 carbon atoms;
    m' is chosen from 0 and 1;
    Y is a group chosen from —COOH, and salts thereof.

2. The method according to claim 1, wherein, in formula (I), $R_1$ is chosen from hydrogen and from methyl, ethyl, propyl and butyl radicals.

3. The method according to claim 1, wherein, in formula (I), Z is chosen from —COO— and —CONH—.

4. The method according to claim 1, wherein, in formula (I), $R_2$ is or comprises a radical chosen from:
  an alkylene radical;
  a phenylene radical —C$_6$H$_4$— (ortho, meta or para) optionally substituted by a C$_1$-C$_{12}$ alkyl radical; and a benzylene radical —C$_6$H$_4$—CH$_2$— optionally substituted by a C$_1$-C$_{12}$ alkyl radical;
  a pyridinium radical of the formula:

wherein $R'_1$ to $R'_4$, which may be identical or different, are chosen from H and C$_1$-C$_{12}$ alkyl radicals;
  a radical of formula —CH$_2$—O—CO—O—, —CH$_2$—CH$_2$—O—CO—O—, —CH$_2$—CO—O—, —CH$_2$—CH$_2$—CO—O—, —CH$_2$—O—CO—NH—, —CH$_2$—CH$_2$—O—CO—NH—, —CH$_2$—NH—CO—NH— and —CH$_2$—CH$_2$—NH—CO—NH—, —CH$_2$—CHOH—, —CH$_2$—CH$_2$—CHOH—, —CH$_2$—CH$_2$—CH(NH$_2$)—, —CH$_2$—CH$_2$—CH(NH$_2$)—, —CH$_2$—CH$_2$—CH(NHR')—, —CH$_2$—CH(NHR')—, —CH$_2$—CH$_2$—CH(NR'R")—, —CH$_2$—CH(NR'R")—, —CH$_2$—CH$_2$—CH$_2$—NR'—, —CH$_2$—CH$_2$—CH$_2$—O— and —CH$_2$—CH$_2$—CHR'—O— wherein R' and R" are chosen from linear and branched C$_1$-C$_{22}$ alkyl;
  and mixtures thereof.

5. The method according to claim 4, whererin, the alkylene radical is chosen from methylene, ethylenic, propylene, n-butylene, isobutylene, tert-butylene, n-hexylene, n-octylene, n-dodecylene, n-octadecylene, n-tetradecylene and n-docosenylene.

6. The method according to claim 1, wherein, in formula (I), n ranges from 5 to 200 inclusive.

7. The method according to claim 6, wherein, in formula (I), n ranges from 9 to 50 inclusive.

8. The method according to claim 1, wherein, in formula (I), $R_3$ is chosen from a hydrogen atom; from mesityl, tosyl, triethoxysilyl, and —$CH_2$—$CH_2CN$ radicals; from benzyl and phenyl radicals optionally substituted by a $C_1$-$C_{12}$ alkyl radical; and $C_1$-$C_{30}$ alkyl radicals from glutarate, mesityl, benzoate, tosyl, triethoxysilane, thioester, benzotriazole carbonate, butyraldehyde, acetaldehyde diethyl acetal, biotin, phospholipid —$SO_3H$, —COOH, and —$PO_4$.

9. The method according to claim 1, wherein the monomer of formula (I) is chosen from:
polyethylene glycol (meth)acrylate;
methylpolyethylene glycol (meth)acrylate;
alkylpolyethylene glycol (meth)acrylates;
phenylpolyethylene glycol (meth)acrylate;
a monomer of:

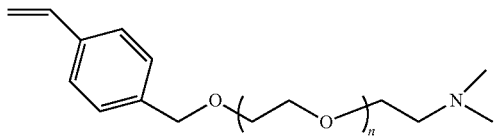

wherein n ranges from 3 to 100 inclusive,
and mixtures thereof.

10. The method according to claim 9, wherein n ranges from 7 to 30 inclusive.

11. The method according to claim 1, wherein the at least one monomer is present in an amount ranging from 20% to 70% by weight, relative to the total weight of the copolymer.

12. The method according to claim 1, wherein the at least one monomer is present in an amount ranging from 30% to 60% by weight, relative to the total weight of the copolymer.

13. The method according to claim 1, wherein, in formula (II), $R_1$ is chosen from hydrogen and from methyl, ethyl, propyl and butyl radicals.

14. The method according to claim 1, wherein, in formula (II), Z' is COO.

15. The method according to claim 1, wherein, in formula (II), $R'_2$ is or comprises a radical chosen from:
an alkylene radical;
a phenylene radical —$C_6H_4$— (ortho, meta or para) optionally substituted by a $C_1$-$C_{12}$ alkyl radical; and a benzylene radical —$C_6H_4$—$CH_2$—optionally substituted by a $C_1$-$C_{12}$ alkyl radical;
a radical of formula —$CH_2$—O—CO—O—, —$CH_2$—$CH_2$—O—CO—O—, —$CH_2$—CO—O—, —$CH_2$—$CH_2$—CO—O—, —$CH_2$—O—CO—NH—, —$CH_2$—$CH_2$—O—CO—NH—, —$CH_2$—NH—CO—NH—, and —$CH_2$—$CH_2$—NH—CO—NH—, —$CH_2$—CHOH—, —$CH_2$—$CH_2$—CHOH—, —$CH_2$—$CH_2$—CH—O— and —$CH_2$—$CH_2$—CHR'—O— wherein R' is chosen from linear and branched $C_1$-$C_{22}$ alkyl radicals;
and mixtures thereof.

16. The method according to claim 15, wherein, the alkylene radical is chosen from methylene, ethylenic, propylene, n-butylene, isobutylene, tert-butylene, n-hexylene, n-octylene, n-dodecylene, n-octadecylene, n-tetradecylene and n-docosenylene.

17. The copolymer according to claim 1, wherein, the at least one anionic monomer is chosen from acrylic acid, methacrylic acid, crotonic acid, itaconic acid, fumaric acid, maleic acid, 2-carboxyethyl acrylate, vinylbenzoic acid, and salts thereof.

18. The method according to claim 17, wherein the salts thereof comprise ammonium salts.

19. The method according to claim 1, wherein the at least one anionic monomer is present in an amount ranging from 30% to 80% by weight, relative to the total weight of the copolymer.

20. The method according to claim 1, wherein the at least one anionic monomer is present in an amount ranging from 40% to 70% by weight, relative to the total weight of the copolymer.

21. The method according to claim 1, wherein the copolymer exhibits a weight-average molecular mass (Mw) ranging from 500 to 5,000,000.

22. The method according to claim 1, wherein the copolymer exhibits a weight-average molecular mass (Mw) ranging from 8,000 to 100,000.

23. The method according to claim 1, wherein the copolymer is conveyed in an aqueous medium.

24. The method according to claim 23, wherein the aqueous medium is water-soluble or water-dispersible.

25. The method accordingly to claim 1, wherein the copolymer exhibits a viscosity in water ranging from 1 mPa·s to 1000 mPa·s, measured at 25° C.

26. The method accordingly to claim 25, wherein the copolymer exhibits a viscosity in water ranging from 2 mPa·s to 500 mPa·s, measured at 25° C.

27. The method according to claim 1, wherein the copolymer exhibits a glass transition temperature (Tg) ranging from −150° C. to 20° C.

28. The method according to claim 1, wherein the copolymer exhibits a glass transition temperature (Tg) ranging from −100° C. to 0° C.

29. The method according to claim 1, wherein the copolymer exhibits a water uptake ranging from 3% to 150% by weight, at 75% relative humidity (75% RH), and/or the copolymer exhibits a water uptake ranging from 5% to 90% by weight, at 85% relative humidity (85% RH).

30. The method according to claim 1, wherein the copolymer exhibits a water uptake ranging from 4.5% to 90% by weight, at 75% relative humidity (75% RH), and/or the copolymer exhibits a water uptake ranging from 15% to 60% by weight, at 85% relative humidity (85% RH).

31. The method according to claim 1, wherein the copolymer has an overall negative charge.

32. The method according to claim 1, wherein the cosmetic composition comprises from 0.1% to 30% by weight on a dry basis, relative to the total weight of the composition of the at least one random ethylenic copolymer.

33. A method for treating hair which comprises applying to the hair, a cosmetic composition comprising, in a physiologically acceptable medium, at least one random ethylenic copolymer consisting of:
a) from 10% to 80% by weight, relative to the total weight of the copolymer, of at least one monomer chosen from compounds of formula (I):

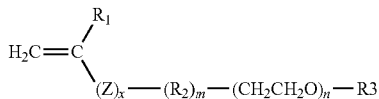

(I)

wherein:
R$_1$ is chosen from a hydrogen atom and linear and branched hydrocarbon radicals of C$_p$H$_{2p+1}$ wherein p is an integer ranging from 1 to 12 inclusive;
Z is a divalent group chosen from —COO—, —CONH—, —CONCH$_3$—, —OCO—, —O—, —SO$_2$—, —CO—O—CO— and —CO—CH$_2$—CO—;
x is chosen from 0 and 1;
R$_2$ is chosen from linear, branched and cyclic, saturated and unsaturated, optionally aromatic, divalent hydrocarbon radicals having from 1 to 30 carbon atoms;
m is 0 or 1;
n is an integer ranging from 3 to 300 inclusive;
R$_3$ is chosen from a hydrogen atom and linear, branched and cyclic, saturated and unsaturated, optionally aromatic, hydrocarbon radical with 1 to 30 carbon atoms; and salts thereof; and
b) from 20% to 90% by weight, relative to the total weight of the copolymer, of an anionic monomer, chosen from monomers of formula (II):

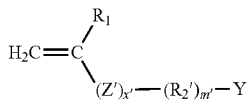

(II)

wherein:
R$_1$ is chosen from a hydrogen atom and linear and branched hydrocarbon radicals C$_p$H$_{2p+1}$ wherein p is an integer ranging from 1 to 12 inclusive;
Z' is a divalent group chosen from —COO—, —OCO— or —O—, —SO$_2$—, —CO—O—CO— and —CO—CH$_2$—CO—;
x' is chosen from 0 and 1;
R'$_2$ is chosen from linear, branched and cyclic, saturated and unsaturated, optionally aromatic, divalent hydrocarbon radicals having 1 to 30 carbon atoms;
m' is chosen from 0 and 1;
Y is a group chosen from COOH and salts thereof,
and optionally at least one additional nonionic hydrophilic monomer chosen from monomers of formula (III):

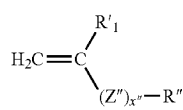

(III)

wherein:
R'$_1$ is chosen from a hydrogen atom and —CH$_3$;
Z'' is a divalent group chosen from —COO—, —CONH—, —CONCH$_3$—, —OCO, —SO$_2$—, —CO—O—CO—, —CO-CH$_2$—CO— or —O—; preferably —COO— and —CONH—;
x'' is chosen from 0 and 1; and
R'' is chosen from linear, branched and cyclic, saturated and unsaturated, optionally aromatic, hydrocarbon radical with 1 to 30 carbon atoms.

34. The method according to claim 33, wherein the cosmetic composition comprises from 0.1% to 30% by weight on a dry basis, relative to the total weight of the composition of the at least one random ethylenic copolymer.

* * * * *